(12) United States Patent
Atiya et al.

(10) Patent No.: US 9,693,839 B2
(45) Date of Patent: Jul. 4, 2017

(54) PROBE HEAD AND APPARATUS FOR INTRAORAL CONFOCAL IMAGING USING POLARIZATION-RETARDING COATINGS

(71) Applicant: Align Technology, Inc., San Jose, CA (US)

(72) Inventors: Yossef Atiya, Maccabim (IL); Tal Verker, Ofra (IL)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 14/334,527

(22) Filed: Jul. 17, 2014

(65) Prior Publication Data

US 2016/0015489 A1 Jan. 21, 2016

(51) Int. Cl.

| | |
|---|---|
| *A61C 9/00* | (2006.01) |
| *G02B 6/27* | (2006.01) |
| *G02B 6/32* | (2006.01) |
| *A61B 1/24* | (2006.01) |
| *A61B 5/00* | (2006.01) |
| *G01B 11/24* | (2006.01) |

(52) U.S. Cl.
CPC .............. *A61C 9/0053* (2013.01); *A61B 1/24* (2013.01); *A61B 5/0068* (2013.01); *A61C 9/0066* (2013.01); *G01B 11/24* (2013.01); *G02B 6/2726* (2013.01); *G02B 6/32* (2013.01)

(58) Field of Classification Search
None
See application file for complete search history.

(56) References Cited

U.S. PATENT DOCUMENTS

| | | | |
|---|---|---|---|
| 2,467,432 | A | 4/1949 | Kesling |
| 3,407,500 | A | 10/1968 | Kesling |
| 3,600,808 | A | 8/1971 | Reeve |

(Continued)

FOREIGN PATENT DOCUMENTS

| | | | |
|---|---|---|---|
| AU | 3031677 A | | 5/1979 |
| AU | 517102 B2 | | 7/1981 |

(Continued)

OTHER PUBLICATIONS

U.S. Appl. No. 14/323,215, filed Jul. 3, 2014, Atiya et al.

(Continued)

*Primary Examiner* — Andrew Jordan
(74) *Attorney, Agent, or Firm* — Wilson Sonsini Goodrich and Rosati

(57) ABSTRACT

A probe head for dental confocal imaging, comprises a light-guiding part for guiding a light beam towards a teeth portion, the light-guiding part having an entrance face through which the light beam enters the light-guiding part and an exit face through which the light beam exits the light-guiding part, wherein the light-guiding part is configured, in case of a linearly polarized light beam having two polarization components being perpendicular to each other, to change polarization of the linearly polarized light beam on its path through the light-guiding part in such a way that one of the two polarization components, compared to the other of the two polarization components, is retarded by an odd multiple of a quarter of a wavelength of the light beam along the path from the entrance face to the exit face.

19 Claims, 2 Drawing Sheets

(56) References Cited

U.S. PATENT DOCUMENTS

| | | |
|---|---|---|
| 3,660,900 A | 5/1972 | Andrews |
| 3,683,502 A | 8/1972 | Wallshein |
| 3,738,005 A | 6/1973 | Cohen |
| 3,860,803 A | 1/1975 | Levine |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,195,046 A | 3/1980 | Kesling |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,478,580 A | 10/1984 | Barrut |
| 4,500,294 A | 2/1985 | Lewis |
| 4,504,225 A | 3/1985 | Yoshii |
| 4,505,673 A | 3/1985 | Yoshii |
| 4,526,540 A | 7/1985 | Dellinger |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,645,704 A * | 2/1987 | Hellwig .................. D06Q 1/04 427/270 |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | van der Zel |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,372,502 A | 12/1994 | Massen et al. |
| 5,382,164 A | 1/1995 | Stern |
| 5,395,238 A | 3/1995 | Andreiko et al. |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern |
| 5,562,448 A | 10/1996 | Mushabac |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre |
| 5,621,648 A | 4/1997 | Crump |
| 5,645,420 A | 7/1997 | Bergersen |
| 5,645,421 A | 7/1997 | Slootsky |
| 5,655,653 A | 8/1997 | Chester |
| 5,659,420 A | 8/1997 | Wakai et al. |
| 5,683,243 A | 11/1997 | Andreiko et al. |
| 5,692,894 A | 12/1997 | Schwartz et al. |
| 5,725,376 A | 3/1998 | Poirier |
| 5,725,378 A | 3/1998 | Wang |
| 5,733,126 A | 3/1998 | Andersson et al. |
| 5,740,267 A | 4/1998 | Echerer et al. |
| 5,742,700 A | 4/1998 | Yoon et al. |
| 5,790,242 A | 8/1998 | Stern et al. |
| 5,799,100 A | 8/1998 | Clarke et al. |
| 5,800,174 A | 9/1998 | Andersson |
| 5,823,778 A | 10/1998 | Schmitt et al. |
| 5,848,115 A | 12/1998 | Little et al. |
| 5,857,853 A | 1/1999 | van Nifterick et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 6,015,289 A | 1/2000 | Andreiko et al. |
| 6,044,309 A | 3/2000 | Honda |
| 6,049,743 A | 4/2000 | Baba |
| 6,062,861 A | 5/2000 | Andersson |
| 6,068,482 A | 5/2000 | Snow |
| 6,099,314 A | 8/2000 | Kopelman et al. |
| 6,123,544 A | 9/2000 | Cleary |
| 6,152,731 A | 11/2000 | Jordan et al. |
| 6,183,248 B1 | 2/2001 | Chishti et al. |
| 6,190,165 B1 | 2/2001 | Andreiko et al. |
| 6,217,325 B1 | 4/2001 | Chishti et al. |
| 6,217,334 B1 | 4/2001 | Hultgren |
| 6,244,861 B1 | 6/2001 | Andreiko et al. |
| 6,309,215 B1 | 10/2001 | Phan et al. |
| 6,315,553 B1 | 11/2001 | Sachdeva et al. |
| 6,322,359 B1 | 11/2001 | Jordan et al. |
| 6,350,120 B1 | 2/2002 | Sachdeva et al. |
| 6,382,975 B1 | 5/2002 | Poirier |
| 6,398,548 B1 | 6/2002 | Muhammad et al. |
| 6,402,707 B1 | 6/2002 | Ernst |
| 6,482,298 B1 | 11/2002 | Bhatnagar |
| 6,524,101 B1 | 2/2003 | Phan et al. |
| 6,554,611 B2 | 4/2003 | Chishti et al. |
| 6,572,372 B1 | 6/2003 | Phan et al. |
| 6,573,998 B2 | 6/2003 | Cohen-Sabban |
| 6,629,840 B2 | 10/2003 | Chishti et al. |
| 6,697,164 B1 * | 2/2004 | Babayoff .................. A61B 1/24 356/601 |

(56) References Cited

U.S. PATENT DOCUMENTS

| | | | |
|---|---|---|---|
| 6,705,863 B2 | 3/2004 | Phan et al. | |
| 6,722,880 B2 | 4/2004 | Chishti et al. | |
| 6,940,611 B2* | 9/2005 | Babayoff | A61B 1/24 356/609 |
| 7,092,107 B2* | 8/2006 | Babayoff | A61B 1/24 356/369 |
| 7,112,065 B2 | 9/2006 | Kopelman | A61C 13/0004 433/213 |
| 7,220,124 B2* | 5/2007 | Taub | A61C 11/001 433/213 |
| 7,230,725 B2* | 6/2007 | Babayoff | A61B 1/24 356/601 |
| 7,450,231 B2* | 11/2008 | Johs | G01N 21/211 356/365 |
| 7,460,230 B2* | 12/2008 | Johs | G02B 27/286 356/365 |
| 7,477,402 B2* | 1/2009 | Babayoff | A61B 1/24 356/601 |
| 7,486,376 B2* | 2/2009 | Kim | G02B 5/305 349/115 |
| 7,488,174 B2* | 2/2009 | Kopelman | A61C 13/0004 433/213 |
| 7,561,273 B2 | 7/2009 | Stautmeister et al. | |
| 7,616,319 B1* | 11/2009 | Woollam | G01J 3/02 356/369 |
| 7,626,705 B2 | 12/2009 | Altendorf | |
| 7,630,089 B2* | 12/2009 | Babayoff | A61B 1/24 356/601 |
| 7,633,625 B1* | 12/2009 | Woollam | G01J 3/02 356/369 |
| 7,719,643 B2* | 5/2010 | Kashima | G02B 5/3016 349/117 |
| 7,791,810 B2 | 9/2010 | Powell | |
| 7,796,277 B2* | 9/2010 | Babayoff | A61B 1/24 356/601 |
| 7,859,622 B2* | 12/2010 | Kashima | G02B 5/3016 349/117 |
| 7,907,280 B2* | 3/2011 | Johs | G02B 5/3083 356/365 |
| 7,942,671 B2* | 5/2011 | Taub | A61C 11/001 433/213 |
| 7,944,569 B2* | 5/2011 | Babayoff | A61B 1/24 356/609 |
| 7,959,308 B2* | 6/2011 | Freeman | G02B 5/1814 353/122 |
| 7,990,548 B2* | 8/2011 | Babayoff | A61B 1/24 356/609 |
| 8,126,025 B2 | 2/2012 | Takeda | |
| 8,310,683 B2* | 11/2012 | Babayoff | A61B 1/24 356/609 |
| 8,451,456 B2 | 5/2013 | Babayoff | |
| 8,454,364 B2* | 6/2013 | Taub | A61C 11/001 433/213 |
| 8,488,113 B2 | 7/2013 | Thiel et al. | |
| 8,577,212 B2 | 11/2013 | Thiel et al. | |
| 8,638,447 B2* | 1/2014 | Babayoff | A61B 1/24 356/609 |
| 8,638,448 B2* | 1/2014 | Babayoff | A61B 1/24 356/609 |
| 8,675,706 B2 | 3/2014 | Seurin et al. | |
| 8,743,923 B2 | 6/2014 | Geske et al. | |
| 8,767,270 B2 | 7/2014 | Curry et al. | |
| 8,878,905 B2* | 11/2014 | Fisker | A61B 5/0068 348/46 |
| 9,089,277 B2* | 7/2015 | Babayoff | A61B 1/24 |
| 9,310,638 B2* | 4/2016 | Choi | G02F 1/133502 |
| 2002/0006597 A1 | 1/2002 | Andreiko et al. | |
| 2003/0009252 A1 | 1/2003 | Pavlovskaia et al. | |
| 2003/0139834 A1 | 7/2003 | Nikolskiy et al. | |
| 2003/0224311 A1 | 12/2003 | Cronauer | |
| 2004/0128010 A1 | 7/2004 | Pavlovskaia et al. | |
| 2005/0055118 A1 | 3/2005 | Nikolskiy et al. | |
| 2005/0080503 A1* | 4/2005 | Kopelman | A61C 13/0004 700/98 |
| 2005/0250075 A1* | 11/2005 | Taub | A61C 11/001 433/213 |
| 2005/0264828 A1* | 12/2005 | Babayoff | A61B 1/24 356/609 |
| 2006/0152656 A1* | 7/2006 | Kashima | G02B 5/3016 349/113 |
| 2006/0158665 A1* | 7/2006 | Babayoff | A61B 1/24 356/609 |
| 2006/0275737 A1* | 12/2006 | Kopelman | A61C 13/0004 433/213 |
| 2007/0046865 A1* | 3/2007 | Umeda | G02B 5/3083 349/96 |
| 2007/0053048 A1* | 3/2007 | Kumar | C07D 311/94 359/241 |
| 2007/0077537 A1* | 4/2007 | Taub | A61C 11/001 433/213 |
| 2007/0109559 A1* | 5/2007 | Babayoff | A61B 1/24 356/609 |
| 2007/0154867 A1* | 7/2007 | Taub | A61C 11/001 433/213 |
| 2007/0166482 A1* | 7/2007 | Kim | G02B 5/305 428/1.1 |
| 2007/0253059 A1* | 11/2007 | Johs | G02B 27/286 359/485.02 |
| 2008/0100842 A1* | 5/2008 | Johs | G01N 21/211 356/369 |
| 2009/0091758 A1* | 4/2009 | Johs | G02B 5/3083 356/369 |
| 2009/0148807 A1* | 6/2009 | Babayoff | A61B 1/24 433/29 |
| 2009/0153879 A1* | 6/2009 | Babayoff | A61B 1/24 356/609 |
| 2009/0218514 A1 | 9/2009 | Klunder et al. | |
| 2010/0045902 A1* | 2/2010 | Ikeda | G02B 5/045 349/96 |
| 2010/0165275 A1* | 7/2010 | Tsukamoto | G02B 5/3083 349/117 |
| 2010/0165357 A1* | 7/2010 | Babayoff | A61B 1/24 356/609 |
| 2010/0165358 A1* | 7/2010 | Babayoff | A61B 1/24 356/609 |
| 2010/0182545 A1* | 7/2010 | Kashima | G02B 5/3016 349/75 |
| 2010/0202034 A1* | 8/2010 | Freeman | G02B 5/1814 359/246 |
| 2011/0183294 A1* | 7/2011 | Taub | A61C 11/001 433/213 |
| 2011/0235045 A1 | 9/2011 | Koerner et al. | |
| 2012/0081786 A1 | 4/2012 | Mizuyama et al. | |
| 2012/0092461 A1* | 4/2012 | Fisker | A61B 5/0068 348/46 |
| 2012/0147912 A1 | 6/2012 | Moench et al. | |
| 2012/0281293 A1 | 11/2012 | Gronenborn et al. | |
| 2013/0094031 A1* | 4/2013 | Babayoff | A61B 1/24 356/609 |
| 2013/0163627 A1 | 6/2013 | Seurin et al. | |
| 2013/0177866 A1* | 7/2013 | Babayoff | A61B 1/24 433/29 |
| 2013/0201488 A1 | 8/2013 | Ishihara | |
| 2013/0266326 A1 | 10/2013 | Joseph et al. | |
| 2013/0293824 A1* | 11/2013 | Yoneyama | B32B 7/12 349/194 |
| 2014/0104620 A1* | 4/2014 | Babayoff | A61B 1/24 356/601 |
| 2015/0064367 A1* | 3/2015 | Choi | G02F 1/133502 428/1.31 |
| 2016/0000332 A1 | 1/2016 | Atiya et al. | |
| 2016/0015489 A1* | 1/2016 | Atiya | A61C 9/0053 433/29 |

(56) References Cited

U.S. PATENT DOCUMENTS

2016/0178821 A1* 6/2016 Choi ............... G02F 1/133502
349/194

FOREIGN PATENT DOCUMENTS

| | | |
|---|---|---|
| AU | 5598894 A | 6/1994 |
| CA | 1121955 | 4/1982 |
| DE | 2749802 | 5/1978 |
| DE | 69327661 T | 7/2000 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 8/1995 |
| EP | 0731673 B1 | 9/1996 |
| EP | 0774933 B1 | 5/1997 |
| EP | 1941843 A2 | 7/2008 |
| EP | 2213223 A1 | 8/2010 |
| EP | 2447754 A1 | 5/2012 |
| ES | 463897 | 1/1980 |
| FR | 2369828 A1 | 6/1978 |
| FR | 2652256 A1 | 3/1991 |
| FR | 2930334 A1 | 10/2009 |
| GB | 15500777 | 8/1979 |
| JP | 53-058191 | 5/1978 |
| JP | 04-028359 | 1/1992 |
| JP | 08-508174 | 9/1996 |
| JP | 2009-018173 A | 1/2009 |
| WO | WO 90/08512 A1 | 8/1990 |
| WO | WO 91/04713 A1 | 4/1991 |
| WO | WO 94/10935 A1 | 5/1994 |
| WO | WO 98/32394 A1 | 7/1998 |
| WO | WO 98/44865 A1 | 10/1998 |
| WO | WO 98/58596 A1 | 12/1998 |
| WO | WO 99/24786 A1 | 5/1999 |
| WO | WO 00/08415 A1 | 2/2000 |
| WO | WO 02/095475 A1 | 11/2002 |
| WO | WO 2007/090865 A1 | 8/2007 |
| WO | WO 2014/091865 A1 | 6/2014 |

OTHER PUBLICATIONS

U.S. Appl. No. 14/323,225, filed Jul. 3, 2014, Atiya et al.
U.S. Appl. No. 14/323,237, filed Jul. 3, 2014, Lampert et al.
U.S. Appl. No. 14/470,832, filed Aug. 27, 2014, Atiya et al.
CEREC Omnicam and CEREC Bluecam brochure. The first choice in every case. The Dental Company Sirona. 2014.
Dummer, et al. Computed Radiography Imaging Based on High-Density 670 nm VCSEL Arrays. Proceedings of SPIE vol. 7557, 75570H (2010)http://vixarinc.com/pdf/SPIE_radiography_manuscript_submission1.pdf.
Pellin Broca Prisms—Specifications. Thor Labs. Updated Nov. 30, 2012. www.thorlabs.com.
International search report and written opinion dated Sep. 25, 2015 for PCT/IB2015/054949.
Invitation to pay additional fees dated Oct. 7, 2015 for PCT/IB2015/054950.
U.S. Appl. No. 14/741,172, filed Jun. 16, 2015, Atiya et al.
AADR. American Association for Dental Research, Summary of Activities, Mar. 20-23, 1980, Los ngeles, CA, p. 195.
Alcaniz, et aL, "An Advanced System for the Simulation and Planning of Orthodontic Treatments," Karl Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.
Alexander et al., "The DigiGraph Work Station Part 2 Clinical Management," JCO, pp. 402-407 (Jul. 1990).
Altschuler et al., "Analysis of 3-D Data for Comparative 3-D Serial Growth Pattern Studies of Oral-Facial Structures," AADR Abstracts, Program and Abstracts of Papers, 57th General Session, IADR Annual Session, Mar. 29, 1979-Apr. 1, 1979, New Orleans Marriot, Journal of Dental Research, vol. 58, Jan. 1979, Special Issue A, p. 221.
Altschuler et al., "Laser Electro-Optic System for Rapid Three-Dimensional (3D) Topographic Mapping of Surfaces," Optical Engineering, 20(6):953-961 (1981).
Altschuler et al., "Measuring Surfaces Space-Coded by a Laser-Projected Dot Matrix," SPIE Imaging q Applications for Automated Industrial Inspection and Assembly, vol. 182, p. 187-191 (1979).
Altschuler, "3D Mapping of Maxillo-Facial Prosthesis," AADR Abstract #607, 2 pages total, (1980).
Andersson et al., "Clinical Results with Titanium Crowns Fabricated with Machine Duplication and Spark Erosion," Acta. Odontol. Scand., 47:279-286 (1989).
Andrews, The Six Keys to Optimal Occlusion Straight Wire, Chapter 3, pp. 13-24 (1989).
Bartels, et al., An Introduction to Splines for Use in Computer Graphics and Geometric Modeling, Morgan Kaufmann Publishers, pp. 422-425 (1987).
Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.
Baumrind et al., "Mapping the Skull in 3-D," reprinted from J. Calif. Dent. Assoc., 48(2), 11 pages total, (1972 Fall Issue).
Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill., Aug. 26-30, 1975, pp. 142-166.
Baumrind, "Integrated Three-Dimensional Craniofacial Mapping: Background, Principles, and Perspectives," Semin in Orthod., 7(4):223-232 (Dec. 2001).
Begole et al., "A Computer System for the Analysis of Dental Casts," The Angle Orthod., 51(3):253-259 (Jul. 1981).
Bernard et al.,"Computerized Diagnosis in Orthodontics for Epidemiological Studies: A ProgressReport," Abstract, J. Dental Res. Special Issue, vol. 67, p. 169, paper presented at International Association for Dental Research 66th General Session, Mar. 9-13, 1988, Montreal, Canada.
Bhatia et al., "A Computer-Aided Design for Orthognathic Surgery," Br. J. Oral Maxillofac. Surg., 22:237-253 (1984).
Biggerstaff et al., "Computerized Analysis of Occlusion in the Postcanine Dentition," Am. J. Orthod., 61(3): 245-254 (Mar. 1972).
Biggerstaff, "Computerized Diagnostic Setups and Simulations," Angle Orthod., 40(1):28-36 (Jan. 1970).
Biostar Opeation & Training Manual. Great Lakes Orthodontics, Ltd. 199 Fire Tower Drive,Tonawanda, New York. 14150-5890, 20 pages total (1990).
Blu, et al., "Linear interpolation revitalized", IEEE Trans. Image Proc., 13(5):710-719 (May 2004).
Bourke, "Coordinate System Transformation," (Jun. 1996), p. 1, retrieved from the Internet Nov. 5, 2004, URL <http://astronomy.swin.edu.au/—pbourke/prolection/coords>.
Boyd et al., "Three Dimensional Diagnosis and Orthodontic Treatment of Complex Malocclusions With the Invisalipn Appliance," Semin Orthod., 7(4):274-293 (Dec. 2001).
Brandestini et al., "Computer Machined Ceramic Inlays: In Vitro Marginal Adaptation," J. Dent. Res. Special Issue, Abstract 305, vol. 64, p. 208 (1985).
Brook et al., "An Image Analysis System for the Determination of Tooth Dimensions from Study Casts: Comparison with Manual Measurements of Mesio-distal Diameter," J. Dent. Res., 65(3):428-431 (Mar. 1986).
Burstone (interview), "Dr. Charles J. Burstone on the Uses of the Computer in Orthodontic Practice (Part 1)," J. Clin. Orthod., 13(7):442-453 (Jul. 1979).
Burstone (interview), "Dr. Charles J. Burstone on the Uses of the Computer in Orthodontic Practice (Part 2)," J. Clin. Orthod., 13(8):539-551 (Aug. 1979).
Burstone et al., Precision Adjustment of the Transpalatal Lingual Arch: Computer Arch Form Predetermination, Am, Journal of Orthodontics, vol. 79, No. 2 (Feb. 1981), pp. 115-133.
Cardinal Industrial Finishes, Powder Coatings information posted at <http://www.cardinalpaint.com> on Aug. 25, 2000, 2 pages.

(56) References Cited

OTHER PUBLICATIONS

Carnaghan, "An Alternative to Holograms for the Portrayal of Human Teeth," 4th Int'l. Conf. on Holographic Systems, Components and Applications, Sep. 15, 1993, pp. 228-231.

Chaconas et al., "The DigiGraph Work Station, Part 1, Basic Concepts," JCO, pp. 360-367 (Jun. 1990).

Chafetz et al., "Subsidence of the Femoral Prosthesis, a Stereophotogrammetric Evaluation," Clin. Orthop. Relat. Res., No. 201, pp. 60-67 (Dec. 1985).

Chiappone, (1980). Constructing the Gnathologic Setup and Positioner, J. Clin. Orthod, vol. 14, pp. 121-133.

Cottingham, (1969). Gnathologic Clear Plastic Positioner, Am. J. Orthod, vol. 55, pp. 23-31.

Crawford, "CAD/CAM in the Dental Office: Does It Work?", Canadian Dental Journal, vol. 57, No. 2, pp. 121-123 (Feb. 1991).

Crawford, "Computers in Dentistry: Part 1: CAD/CAM: The Computer Moves Chairside," "Part 2: F. Duret—A Man With a Vision," "Part 3: The Computer Gives New Vision-Literally," "Part 4: Bytes 'N Bites" The Computer Moves From the Front Desk to the Operatory, Canadian Dental Journal, vol. 54(9), pp. 661-666 (1988).

Crooks, "CAD/CAM Comes to USC," USC Dentistry, pp. 14-17 (Spring 1990).

Cureton, Correcting Malaligned Mandibular Incisors with Removable Retainers, J. Clin. Orthod, vol. 30, No. 7 (1996) pp. 390-395.

Curry et al., "Integrated Three-Dimensional Craniofacial Mapping at the Craniofacial Research Instrumentation Laboratory/University of the Pacific," Semin Orthod., 7(4):258-265 (Dec. 2001).

Cutting et al., "Three-Dimensional Computer-Assisted Design of Craniofacial Surgical Procedures: Optimization and Interaction with Cephalometric and CT-Based Models," Plast. 77(6):877-885 (Jun. 1986).

DCS Dental AG, "The CAD/CAM 'DCS Titan System' for Production of Crowns/Bridges," DSC Production, pp. 1-7 (Jan. 1992).

Definition for gingiva. Dictionary.com p. 1-3. Retrieved from the internet Nov. 5, 2004 <http://reference.com/search/search?q=gingiva>.

DeFranco et al., "Three-Dimensional Large Displacement Analysis of Orthodontic Appliances," J. Biomechanics, 9:793-801 (1976).

Dental Institute University of Zurich Switzerland, Program for International Symposium on Computer Restorations: State of the Art of the CEREC-Method, May 1991, 2 pages total.

Dentrac Corporation, Dentrac document, pp. 4-13 (1992).

DENT-X posted on Sep. 24, 1998 at <http://www.dent-x.com/DentSim.htm>, 6 pages.

Doyle, "Digital Dentistry," Computer Graphics World, pp. 50-52, 54 (Oct. 2000).

DuraClearTM product information, Allesee Orthodontic Appliances-Pro Lab, 1 page (1997).

Duret et al, "CAD-CAM in Dentistry," J. Am. Dent. Assoc. 117:715-720 (Nov. 1988).

Duret et al., "CAD/CAM Imaging in Dentistry," Curr. Opin. Dent., 1:150-154 (1991).

Duret, "The Dental CAD/CAM, General Description of the Project," Hennson International Product Brochure, 18 pages total, Jan. 1986.

Duret,"Vers Une Prosthese Informatisee," (English translation attached), Tonus, vol. 75, pp. 55-57 (Nov. 15, 1985).

Economides, "The Microcomputer in the Orthodontic Office," JCO, pp. 767-772 (Nov. 1979).

Elsasser, Some Observations on the History and Uses of the Kesling Positioner, Am. J. Orthod. (1950) 36:368-374.

English translation of Japanese Laid-Open Publication No. 63-11148 to inventor T. Ozukuri (Laid-Open on Jan. 18, 1998) pp. 1-7.

Felton et al., "A Computerized Analysis of the Shape and Stability of Mandibular Arch Form," Am. J. Orthod. Dentofacial Orthop., 92(6):478-483 (Dec. 1987).

Friede et al., "Accuracy of Cephalometric Prediction in Orthognathic Surgery," Abstract of Papers, J. Dent. Res., 70:754-760 (1987).

Futterling et a/., "Automated Finite Element Modeling of a Human Mandible with Dental Implants," JS WSCG '98—Conference Program, retrieved from the Internet: <http://wscg.zcu.cz/wscg98/papers98/Strasser 98.pdf>, 8 pages.

Gao et al., "3-D element Generation for Multi-Connected Complex Dental and Mandibular Structure," Proc. Intl Workshop on Medical Imaging and Augmented Reality, pp. 267-271 (Jun. 12, 2001).

Gim-Alldent Deutschland, "Das DUX System: Die Technik," 2 pages total (2002).

Gottleib et al., "JCO Interviews Dr. James A. McNamara, Jr., on the Frankel Appliance: Part 2: Clinical 1-1 Management,"J. Clin. Orthod., 16(6):390-407 (Jun. 1982).

Grayson, "New Methods for Three Dimensional Analysis of Craniofacial Deformity, Symposium: Computerized Facial Imaging in Oral and Maxiiofacial Surgery," AAOMS, 3 pages total, (Sep. 13, 1990).

Guess et al., "Computer Treatment Estimates in Orthodontics and Orthognathic Surgery," JCO, pp. 262-28 (Apr. 1989).

Heaven et al. "Computer-Based Image Analysis of Artificial Root Surface Caries," Abstracts of Papers, J. Dent. Res., 70:528 (Apr. 17-21, 1991).

Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingampproduction/november011996/simulatingstressputonfa . . . >.

Hikage, "Integrated Orthodontic Management System for Virtual Three-Dimensional Computer Graphic Simulation and Optical Video Image Database for Diagnosis and Treatment Planning", Journal of Japan KA Orthodontic Society, Feb. 1987, English translation, pp. 1-38, Japanese version, 46(2), pp. 248-269 (60 pages total).

Hoffmann, et al., "Role of Cephalometry for Planning of Jaw Orthopedics and Jaw Surgery Procedures," (Article Summary in English, article in German), Informatbnen, pp. 375-396 (Mar. 1991).

Hojjatie et al., "Three-Dimensional Finite Element Analysis of Glass-Ceramic Dental Crowns," J. Biomech., 23(11):1157-1166 (1990).

Huckins, "CAD-CAM Generated Mandibular Model Prototype from MRI Data," AAOMS, p. 96 (1999).

Important Tip About Wearing the Red White & Blue Active Clear Retainer System, Allesee Orthodontic Appliances-Pro Lab, 1 page 1998).

JCO Interviews, Craig Andreiko , DDS, MS on the Elan and Orthos Systems, JCO, pp. 459-468 (Aug. 1994).

JCO Interviews, Dr. Homer W. Phillips on Computers in Orthodontic Practice, Part 2, JCO. 1997; 1983:819-831.

Jerrold, "The Problem, Electronic Data Transmission and the Law," AJO-DO, pp. 478-479 (Apr. 1988).

Jones et al., "An Assessment of the Fit of a Parabolic Curve to Pre- and Post-Treatment Dental Arches," Br. J. Orthod., 16:85-93 (1989).

JP Faber et al., "Computerized Interactive Orthodontic Treatment Planning," Am. J. Orthod., 73(1):36-46 (Jan. 1978).

Kamada et.al., Case Reports on Tooth Positioners Using LTV Vinyl Silicone Rubber, J. Nihon University School of Dentistry (1984) 26(1): 11-29.

Kamada et.al., Construction of Tooth Positioners with LTV Vinyl Silicone Rubber and Some Case KJ Reports, J. Nihon University School of Dentistry (1982) 24(1):1-27.

Kanazawa et al., "Three-Dimensional Measurements of the Occlusal Surfaces of Upper Molars in a Dutch Population," J. Dent Res., 63(11):1298-1301 (Nov. 1984).

Kesling et al., The Philosophy of the Tooth Positioning Appliance, American Journal of Orthodontics and Oral surgery. 1945; 31:297-304.

Kesling, Coordinating the Predetermined Pattern and Tooth Positioner with Conventional Treatment, Am. J. Orthod. Oral Surg. (1946) 32:285-293.

Kleeman et al., The Speed Positioner, J. Clin. Orthod. (1996) 30:673-680.

(56) References Cited

OTHER PUBLICATIONS

Kochanek, "Interpolating Splines with Local Tension, Continuity and Bias Control," Computer Graphics, 18(3):33-41 (Jul. 1984).
Oral Surgery (1945) 31 :297-30.
Kunii et al., "Articulation Simulation for an Intelligent Dental Care System," Displays 15:181-188 (1994).
Kuroda et al., Three-Dimensional Dental Cast Analyzing System Using Laser Scanning, Am. J. Orthod. Dentofac. Orthop. (1996) 110:365-369.
Laurendeau, et al., "A Computer-Vision Technique for the Acquisition and Processing of 3-D Profiles of 7 Dental Imprints: An Application in Orthodontics," IEEE Transactions on Medical Imaging, 10(3):453-461 (Sep. 1991).
Leinfelder, et al., "A New Method for Generating Ceramic Restorations: a CAD-CAM System," J. Am. 1-1 Dent. Assoc., 118(6):703-707 (Jun. 1989).
Manetti, et al., "Computer-Aided Cefalometry and New Mechanics in Orthodontics," (Article Summary in English, article in German), Fortschr Kieferorthop. 44, 370-376 (Nr. 5), 1983.
McCann, "Inside the ADA," J. Amer. Dent. Assoc., 118:286-294 (Mar. 1989).
McNamara et al., "Invisible Retainers," J. Cfin. Orthod., pp. 570-578 (Aug. 1985).
McNamara et al., Orthodontic and Orthopedic Treatment in the Mixed Dentition, Needham Press, pp. 347-353 (Jan. 1993).
Moermann et al., "Computer Machined Adhesive Porcelain Inlays: Margin Adaptation after Fatigue Stress," IADR Abstract 339, J. Dent. Res., 66(a):763 (1987).
Moles, "Correcting Mild Malalignments—As Easy As One, Two, Three," AOA/Pro Corner, vol. 11, No. 1, 2 pages (2002).
Mormann et al., "Marginale Adaptation von adhasuven Porzellaninlays in vitro," Separatdruck aus:Schweiz. Mschr. Zahnmed. 95: 1118-1129, 1985.
Nahoum, "The Vacuum Formed Dental Contour Appliance," N. Y. State Dent. J., 30(9):385-390 (Nov. 1964).
Nash, "CEREC CAD/CAM Inlays: Aesthetics and Durability in a Single Appointment," Dent. Today, 9(8):20, 22-23 (Oct. 1990).
Nishiyama et al., "A New Construction of Tooth Repositioner by LTV Vinyl Silicone Rubber," J. Nihon Univ. Sch. Dent., 19(2):93-102 (1977).
Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.
Pinkham, "Foolish Concept Propels Technology," Dentist, 3 pages total, Jan./Feb. 1989.
Pinkham, "Inventor's CAD/CAM May Transform Dentistry," Dentist, 3 pages total, Sep. 1990.
Ponitz, "Invisible Retainers," Am. J. Orthod., 59(3):266-272 (Mar. 1971).
PROCERA Research Projects, "PROCERA Research Projects 1993—Abstract Collection," pp. 3-7 28 (1993).
Proffit et al., Contemporary Orthodontics, (Second Ed.), Chapter 15, Mosby Inc., pp. 470-533 (Oct. 1993).
Raintree Essix & ARS Materials, Inc., Raintree Essix, Technical Magazine Table of contents and Essix Appliances, <http://www.essix.com/magazine/defaulthtml> Aug. 13, 1997.
Redmond et al., "Clinical Implications of Digital Orthodontics," Am. J. Orthod. Dentofacial Orthop., 117(2):240-242 (2000).
Rekow et al. "CAD/CAM for Dental Restorations—Some of the Curious Challenges," IEEE Trans. Biomed. Eng., 38(4):314-318 (Apr. 1991).
Rekow et al., "Comparison of Three Data Acquisition Techniques for 3-D Tooth Surface Mapping," Annual International Conference of the IEEE Engineering in Medicine and Biology Society, 13(1):344-345 1991.
Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).
Rekow, "CAD/CAM in Dentistry: A Historical Perspective and View of the Future," J. Can. Dent. Assoc., 58(4):283, 287-288 (Apr. 1992).
Rekow, "Computer-Aided Design and Manufacturing in Dentistry: A Review of the State of the Art," J. Prosthet. Dent., 58(4):512-516 (Oct. 1987).
Rekow, "Dental CAD-CAM Systems: What is the State of the Art?", J. Amer. Dent. Assoc., 122:43-48 1991.
Rekow, "Feasibility of an Automated System for Production of Dental Restorations, Ph.D. Thesis," Univ. of Minnesota, 244 pages total, Nov. 1988.
Richmond et al., "The Development of a 3D Cast Analysis System," Br. J. Orthod., 13(1):53-54 (Jan. 1986).
Richmond et al., "The Development of the PAR Index (Peer Assessment Rating): Reliability and Validity," Eur. J. Orthod., 14:125-139 (1992).
Richmond, "Recording the Dental Cast in Three Dimensions," Am. J. Orthod. Dentofacial Orthop., 92(3):199-206 (Sep. 1987).
Rudge, "Dental Arch Analysis: Arch Form, a Review of the Literature," Eur. J. Orthod., 3(4):279-284 1981.
Sakuda et al., "Integrated Information-Processing System in Clinical Orthodontics: An Approach with Use of a Computer Network System," Am. J. Orthod. Dentofacial Orthop., 101(3): 210-220 (Mar. 1992).
Schellhas et al., "Three-Dimensional Computed Tomography in Maxillofacial Surgical Planning," Arch. Otolamp!. Head Neck Surg., 114:438-442 (Apr. 1988).
Schroeder et al., Eds. The Visual Toolkit, Prentice Hall PTR, New Jersey (1998) Chapters 6, 8 & 9, (pp. 153-210,309-354 and 355-428, respectively).
Shilliday, (1971). Minimizing finishing problems with the minipositioner, Am. J. Orthod. 59:596-599.
Siemens, "CEREC—Computer-Reconstruction," High Tech in der Zahnmedizin, 14 pages total (2004).
Sinclair, "The Readers' Corner," J. Clin. Orthod., 26(6):369-372 (Jun. 1992).
Sirona Dental Systems GmbH, CEREC 3D, Manuel utiiisateur, Version 2.0X (in French), 2003,114 pages total.
Stoll et al., "Computer-aided Technologies in Dentistry," (article summary in English, article in German), Dtsch Zahna'rztl Z 45, pp. 314-322 (1990).
Sturman, "Interactive Keyframe Animation of 3-D Articulated Models," Proceedings Graphics Interface '84, May-Jun. 1984, pp. 35-40.
The Choice Is Clear: Red, White & Blue . . . The Simple, Affordable, No-Braces Treatment, Allesee Orthodontic Appliances—Pro Lab product information for doctors. http://ormco.com/aoa/appliances-services/RWB/doctorhtml>, 5 pages (May 19, 2003).
The Choice is Clear: Red, White & Blue . . . The Simple, Affordable, No-Braces Treatment, Allesee Orthodontic Appliances—Pro Lab product information for patients, <http://ormco.com/aoa/appliancesservices/RWB/patients.html>, 2 pages (May 19, 2003).
The Choice Is Clear: Red, White & Blue . . . The Simple, Affordable, No-Braces Treatment, Allesee Orthodontic Appliances—Pro Lab product information, 6 pages (2003).
The Red, White & Blue Way to Improve Your Smile! Allesee Orthodontic Appliances—Pro Lab product information for patients, 2 pages 1992.
Truax L., "Truax Clasp-Less(TM) Appliance System," Funct. Orthod., 9(5):22-4, 26-8 (Sep.-Oct. 1992).
Tru-Tain Orthodontic & Dental Supplies, Product Brochure, Rochester, Minnesota 55902, 16 pages total (1996).
U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.

(56) References Cited

OTHER PUBLICATIONS

U.S. Appl. No. 60/050,342, filed Jun. 20, 1997, 41 pages total.
Van Der Linden et al., "Three-Dimensional Analysis of Dental Casts by Means of the Optocom," J. Dent. Res., p. 1100 (Jul.-Aug. 1972).
Van Der Linden, "A New Method to Determine Tooth Positions and Dental Arch Dimensions," J. Dent. Res., 51(4):1104 (Jul.-Aug. 1972).
Van Der Zel, "Ceramic-Fused-to-Metal Restorations with a New CAD/CAM System," Quintessence Int., 24(11):769-778 (1993).
Varady et al., "Reverse Engineering of Geometric Models—An Introduction," Computer-Aided Design, 29(4):255-268,1997.
Verstreken et al., "An Image-Guided Planning System for Endosseous Oral Implants," IEEE Trans. Med. Imaging, 17(5):842-852 (Oct. 1998).
Warunek et al., Physical and Mechanical Properties of Elastomers in Orthodonic Positioners, Am J. Orthod. Dentofac. Orthop, vol. 95, No. 5, (May 1989) pp. 399-400.
Warunek et.al., Clinical Use of Silicone Elastomer Applicances, JCO (1989) XXIII(10):694-700.
Wells, Application of the Positioner Appliance in Orthodontic Treatment, Am. J. Orthodont. (1970) 58:351-366.
328 . Williams, "Dentistry and CAD/CAM: Another French Revolution," J. Dent. Practice Admin., pp. 2-5 (Jan./Mar. 1987).
Williams, "The Switzerland and Minnesota Developments in CAD/CAM," J. Dent. Practice Admin., pp. 50-55 (Apr./Jun. 1987).
Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990.
WSCG'98—Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.
Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).
Yamamoto et al., "Optical Measurement of Dental Cast Profile and Application to Analysis of Three-Dimensional Tooth Movement in Orthodontics," Front. Med. Biol. Eng., 1(2):119-130 (1988).
Yamamoto et al., "Three-Dimensional Measurement of Dental Cast Profiles and Its Applications to Orthodontics," Conf. Proc. IEEE Eng. Med. Biol. Soc., 12(5):2051-2053 (1990).
Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.
Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).
Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).
Yoshii, "Research on a New Orthodontic Appliance: The Dynamic Positioner (D.P.); Ill.—The General Concept of the D.P. Method and Its Therapeutic Effect, Part 2. Skeletal Reversed Occlusion Case Reports," Nippon Dental Review, 458:112-129 (Dec. 1980).
Yoshii, "Research on a New Orthodontic Appliance: The Dynamic Positioner (D.P.); Ill. The General Concept of the D.P. Method and Its Therapeutic Effect, Part 1, Dental and Functional Reversed Occlusion Case Reports," Nippon Dental Review, 457:146-164 (Nov. 1980).
You May Be a Candidate for This Invisible No-Braces Treatment, Allesee Orthodontic Appliances-Pro Lab product information for patients, 2 pages (2002).
International search report and written opinion dated Jan. 4, 2016 for PCT/IB2015/054950.

* cited by examiner

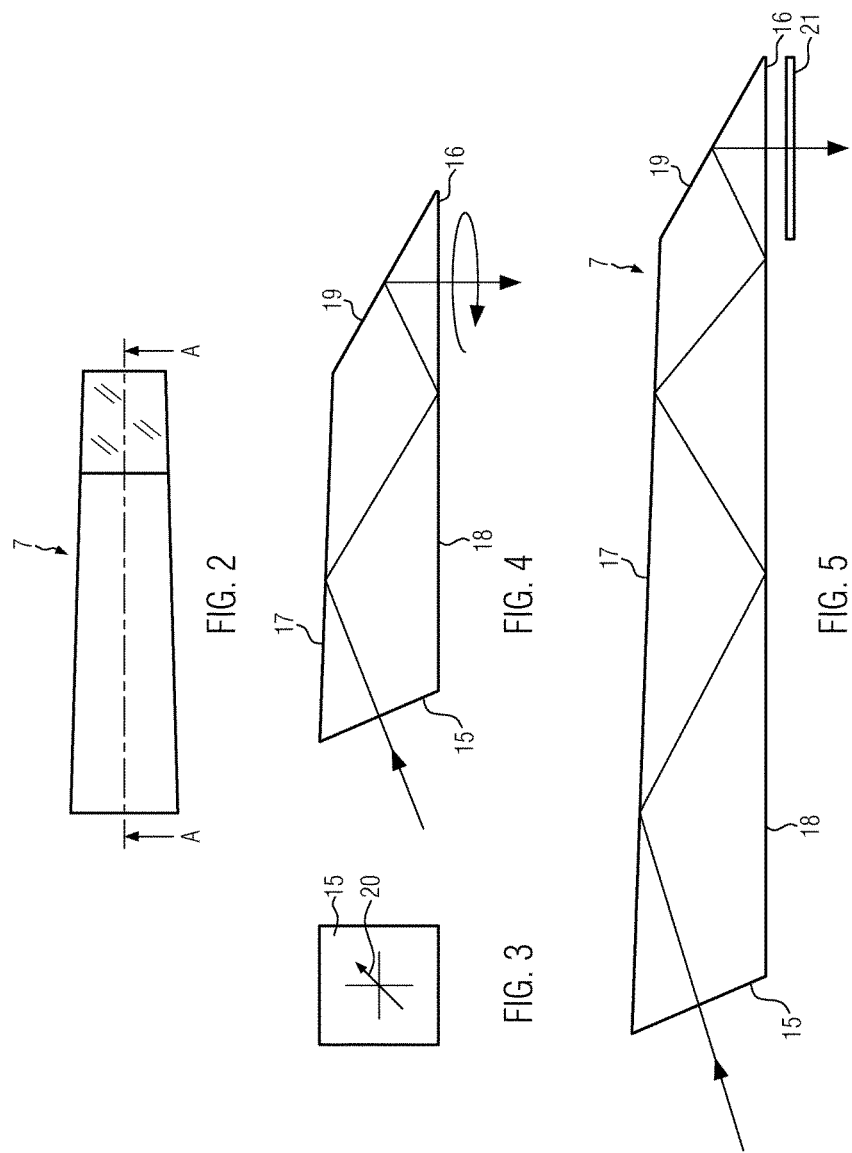

PROBE HEAD AND APPARATUS FOR INTRAORAL CONFOCAL IMAGING USING POLARIZATION-RETARDING COATINGS

FIELD

The present disclosure is directed to a probe head for intraoral confocal imaging and an apparatus comprising the same, particularly useful for surveying of teeth.

BACKGROUND

In the fields of orthodontics and prosthodontics, different methods are known to determine a current teeth topology in a patient's mouth. One of the methods involves taking an impression of a patient's dentition. Using this impression, a plaster cast is made, representing a (positive) physical teeth model. This physical teeth model may then be used for a subsequent treatment plan.

If CAD (computer-aided design) and/or CAM (computer-aided manufacturing) techniques are to be employed, a digital dataset corresponding to the teeth may be obtained by scanning For example, the (positive) physical teeth model in form of the plaster cast or a (negative) physical teeth model in form of the impression may be scanned or imaged using x-rays, computed tomography, magnetic resonance imaging, or laser scanning apparatuses. With the thus obtained image data, a computer model of the teeth or a part thereof may be established. However, such methods and apparatus can be somewhat time consuming and more expensive than would be ideal.

As an alternative, teeth in a patient's mouth may be imaged directly. For this purpose, different imaging apparatuses are known.

The prior apparatus for non-contact imaging with a probe having a sensing face have been less than ideal in at least some respects. The prior probe devices can be somewhat larger than would be ideal, and may have a large intraoral front tip which can make the prior devices somewhat cumbersome to use in at least some instances. Although an array of incident light beams passing through focusing optics can be used, the larger than ideal probe heads of such devices can provide less than ideal measurements of the oral cavity of a patient. Also, the prior devices that rely on beams to generate illuminated spots on the structure and the intensity of returning light rays propagating along an optical path can be somewhat cumbersome to use and maintain and can be somewhat more costly to manufacture than would be ideal.

Although quarter wave plates (QWPs) have been used with prior devices, the prior QWPs can provide less than ideal results in at least some instances. For example, disposable QWPs can have less than ideal quality and can be less available than would be ideal. Although fixed QWPs have been proposed, the alignment and reliability of fixed QWPs can be less than ideal. Also, the use of QWPs can be associated with less than ideal numerical apertures and accuracy, and may be less than ideally suited for combination with telecentric measurement systems. Also, the use of QWPs can provide an additional optical component that can be related to less than ideal control of contamination, for example.

Although three dimensional (3D) data acquisition using triangulation has been proposed, such devices can be less compact than would be ideal and can be somewhat difficult to place in the mouth of the patient. Also, such devices can require alignment and can be less accurate and reliable than would be ideal in at least some instances.

In light of the above, improved methods and apparatus for measuring surfaces such as the intraoral cavity are needed. Ideally such methods and apparatus will overcome at least some of the deficiencies of the prior methods and apparatus and be more accurate, reliable, compact, easier to use with the patient's mouth and less costly than the prior devices.

SUMMARY

In accordance with embodiments, a probe head for dental focal imaging is provided, comprising a light-guiding part for guiding a light beam towards a teeth portion, the light-guiding part having an entrance face through which the light beam enters the light-guiding part and an exit face through which the light beam exits the light-guiding part. The light-guiding part may be configured to provide a relative retardance of polarization components comprising an odd multiple of a quarter of a wavelength of the light beam along the path from the entrance face to the exit face. In many embodiments, a linearly polarized light beam having two polarization components being perpendicular to each other provides a change in polarization of the linearly polarized light beam on its path through the light-guiding part in such a way that one of the two polarization components, as compared to the other of the two polarization components, is retarded by an odd multiple of a quarter of a wavelength of the light beam along the path from the entrance face to the exit face. The reflecting surfaces of the probe head can be arranged and/or configured in one or more of many ways so as to provide the relative retardance of the odd integer multiple of the quarter of the wavelength. In many embodiments, the angles of the reflecting surfaces are arranged to provide the retardance. Alternatively or in combination, coatings can be provided on one or more surfaces to provide the retardance. In many embodiments, the angles of the surfaces provide a first portion of the retardance and the one or more coatings provide a second portion of the retardance, and the first portion combined with the second portion provides a combined total relative retardance between the entrance face and the exit face comprising the odd integer multiple of the quarter of the wavelength. The first portion can comprise a first non-integer multiple of a quarter of the wavelength; the second portion can comprise a second non-integer multiple of the quarter of the wavelength. In many embodiments, a reflective coating at the front end of the probe can provide the full ¼wave retardation, when complemented with the existing retardation induced by reflection at the other surfaces. The coating may comprise a plurality of layers comprising a low index layer, a high index layer and a medium index layer. In many embodiments the plurality of layers comprises a plurality of low index layers, a plurality of high index layers and a plurality of medium index layers. The retardance comprising an odd multiple of the quarter wavelength has the advantage of providing returning light that has been phase shifted by a half wavelength and a corresponding 90 degree rotation of linearly polarized light, which can be used with a polarizing beam splitter in order to increase energy efficiency of the measurement apparatus.

Other objects and features of the present invention will become apparent by a review of the specification, claims, and appended figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2 shows a top view of a schematically illustrated probe head, in accordance with many embodiments;

FIG. 3 shows a plan view of the entrance face of a schematically illustrated probe head, in accordance with many embodiments;

FIG. 4 shows a longitudinal cross-section through line A-A in FIG. 2, in accordance with many embodiments; and FIG. 5 shows a longitudinal cross-section through a schematically illustrated probe head, in accordance with many embodiments.

DETAILED DESCRIPTION

Figure 1:
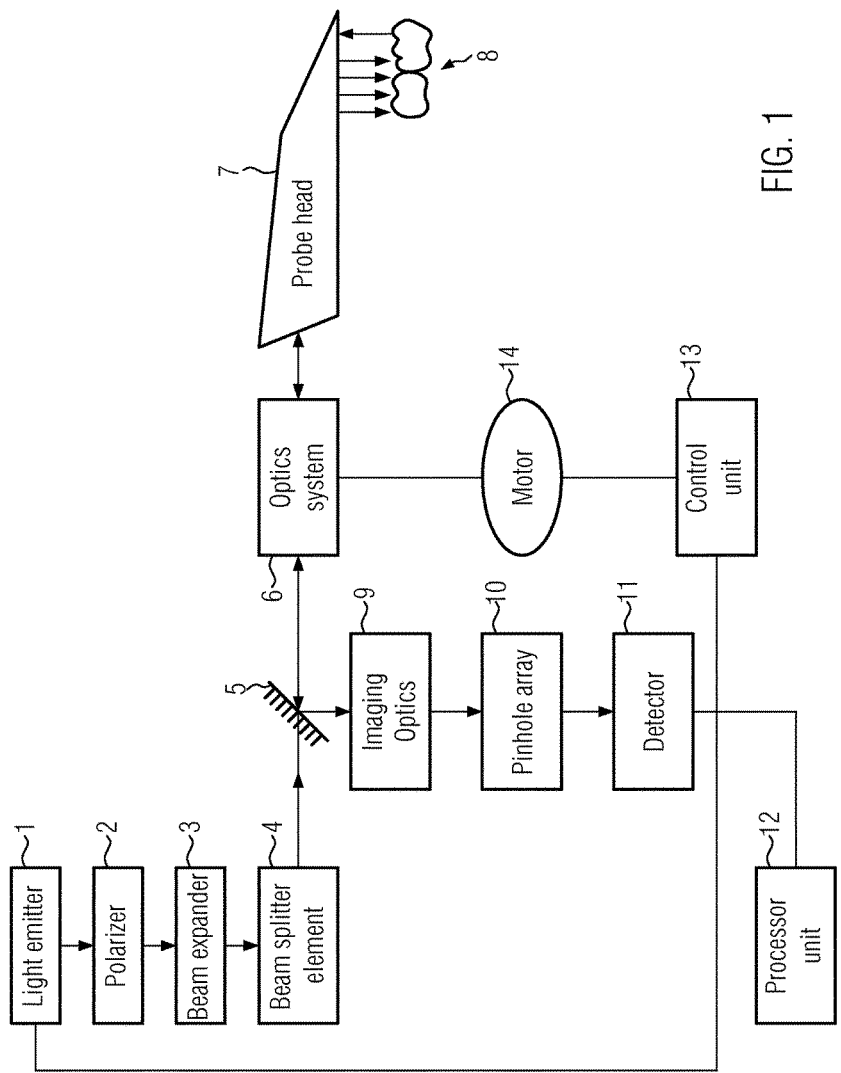
FIG. 1 shows a schematic view of a confocal imaging apparatus, in accordance with many embodiments.

The methods and apparatus disclosed herein can be combined in one or more of many ways and are well suited for combination with many devices related to surface topology such as the measurement of tissue surfaces such as surfaces of the oral cavity. The tissue surfaces may comprise one or more surfaces of teeth of the mouth, for example. The measured surfaces can be used by health care providers such as orthodontists and dentists.

As used herein and/or encompasses alternative elements and combinations of elements. For example, A and/or B encompasses A alone, B alone, and combinations of A and B.

As used herein lambda ("$\lambda$") indicates the wavelength of light of a light beam.

In many embodiments, a linearly polarized light beam (having two polarization components being perpendicular to each other) may undergo a change of polarization along its path from the entrance face of the light-guiding part to the exit face thereof. A QWP may change the polarization as well. Providing the polarization change with the probe itself can be beneficial for additional reasons such as decreased size, fewer system elements, and decreased cost. A retardance by an odd integer multiple of a quarter of the wavelength may correspond to a phase shift of an odd multiple of $\pi/2$, for example.

The light-guiding part may be configured such that a linear polarization of a light beam at the entrance face is changed to one or more of elliptical polarization or circular polarization at the exit face.

In many embodiments, the probe provides the phase retardance comprising an odd multiple of quarter wavelength and can be used in a manner similar to a quarter wave plate by using linearly polarized light in the system. The phase of linear polarization which goes through the probe is retarded by a quarter of wavelength and thus circularly polarized. When reflected back from the object such as a tooth and going through the probe in the opposite direction, an additional quarter wavelength retardation occurs and the polarization is linear and 90 degrees to the original polarization. By using a polarization beam splitter, the optical power transmission efficiency of the system can be increased substantially, for example maximized.

The light beam may comprise a polychromatic light beam (i.e. having a range of wavelengths) or a monochromatic light beam (i.e. having a single wavelength, e.g. as obtained from a laser source).

The probe head may be configured for intraoral confocal imaging, such as a probe head for intraoral confocal imaging, and/or for confocal imaging of positive and/or negative physical teeth models.

The light-guiding part may comprise a transparent body and/or a one-piece body. For example, the transparent body may comprise glass or plastics and may comprise a solid body. In many embodiments the transparent body comprises a stiff body, such as a rigid body.

The light-guiding part may be bounded by sidewalls, and one or more of the sidewalls may comprise a retardance coating such that the total retardance of the one of the two polarization components, with respect to the other polarization component, along the path from the entrance face to the exit face is an odd multiple of a quarter of the wavelength. In this way, a phase shift of the one polarization component by an odd multiple of $\pi/2$ can be achieved, so as to provide the advantages as described herein. Each of the sidewalls and/or the exit face and/or the entrance face may be planar, for example.

The light-guiding part may be bounded by sidewalls and the light-guiding part may be configured and/or arranged such that the light beam entering through the entrance face is reflected from at least one of the sidewalls of the light-guiding part by way of total internal reflection. The above-mentioned retardance coating may lead to a change or modification of the total internal reflection conditions, particularly as regards a phase shift of one of the two polarization components. In many embodiments, retardance coating as described herein may be provided at a sidewall or at part of a sidewall where the light beam is reflected by way of total internal reflection. In many embodiments, the light-guiding part comprises angles and an index of refraction arranged to provide total internal reflection.

Alternatively or additionally to total internal reflection, one or more reflections may be provided with a mirror coating of a sidewall or of part of a sidewall. The retardance coating may provide a change or modification of the mirror reflection conditions, for example with respect to a phase shift of one of the two polarization components. In many embodiments, the retardance coating as described herein may be provided at a sidewall or at part of a sidewall where the light beam is reflected by way of mirror reflection, for example.

The light-guiding part may comprise an upper sidewall arranged at an acute angle with respect to the entrance face, a lower sidewall arranged at an obtuse angle with respect to the entrance face, and an end sidewall arranged at an acute angle with respect to the entrance face and/or the exit face. The upper sidewall may adjoin the entrance face, the lower sidewall may adjoin the entrance face and/or the end sidewall may join the upper sidewall and/or the lower sidewall, for example. The angle between the end sidewall and the upper sidewall may be an obtuse angle. The lower sidewall may comprise the exit face.

The end sidewall may comprise a mirror. For example, the end sidewall may comprise a mirror coating. In such embodiments, the light-guiding part may be arranged and/or configured such that a light beam entering through the entrance face is reflected at all sidewalls except for the end sidewall by way of total internal reflection. The angle between the entrance face and the lower sidewall may lie between 90° and 125°, in particular, between 90° and 115°. The angle between the exit face or the lower sidewall and the end sidewall may lie between 20° and 45°, in particular, between 25° and 35°. The angle between the entrance face and the upper sidewall may lie between 90° and 65°, in particular, between 90° and 80°.

The embodiments also provide an apparatus for dental confocal imaging, comprising an illumination module for generating an array of light beams, an optics system for confocal focusing of the array of light beams and a probe head as described above, wherein the illumination module, the optics system and the probe head are arranged such that the array of light beams from the illumination module passes through the optics system, enters the light-guiding part by the entrance face and exists the light-guiding part by the exit face. In particular, the light-guiding part may be arranged such that the above-described change of the polarization of the linearly polarized light beam is achieved.

The apparatus may be configured for intraoral confocal imaging, and may comprise an apparatus for intraoral confocal imaging, and/or for confocal imaging of positive and/or negative physical teeth models, for example. The apparatus may comprise a scanning apparatus. The focusing optics of the apparatus may comprise telecentric or non-telecentric optics, for example.

The light-guiding part may be arranged such that the array of light beams enters the light-guiding part at an angle of about 90° with respect to the entrance face. In many embodiments, the light guiding part may be arranged such that the array of light beams enters via the entrance face at an angle of 90°±5°, for example 90°±3°.

The light-guiding part may be bounded by sidewalls and the light-guiding part may be arranged and/or configured such that each light beam entering the light-guiding part through the entrance face is reflected at the sidewalls an odd number of times before exiting through the exit face. In many embodiments, each light beam may be reflected at the sidewalls three or five times before exiting through the exit face, for example.

The illumination module may comprise a single light emitter or a plurality of light emitters, for example. The one or more light emitters may emit coherent light. In many embodiments, the light emitter may comprise a single laser emitter or a plurality of laser emitters. The light emitter may comprise the single light emitter, and the illumination module may further comprise a beam expander element and/or a beam splitter element for splitting a light beam from the light emitter into a plurality of light beams and/or an array of light beams, for example. The beam splitter element may comprise diffractive optics, or refractive optics, and combinations thereof, for example. For example, the beam splitter element may comprise a grating or a microlens array.

Any of the apparatuses and methods as described herein may comprise a polarizer for linearly polarizing a light beam, in which polarizer is arranged along the optical path between the illumination module and the probe head. In many embodiments, the polarizer is arranged between the illumination module and the optics system. The polarizer may be configured and/or arranged such that the polarization plane of a light beam passing through the entrance face of the light-guiding part is not parallel to the symmetry plane of the light-guiding part (i.e., the polarization plane is tilted with respect to the symmetry plane). The symmetry plane may be arranged in parallel to the plane in which the optical path is located.

Any of the methods and apparatuses as described herein may comprise a beam splitter arranged along the optical path between the illumination module and the optics system such that the array of light beams from the illumination module passes through the beam splitter, and such that an array of returning light beams from the optics module is reflected, in particular, towards a detector. The beam splitter may comprise a semi-transparent mirror, for example. The light beams coming from the illumination module passing through the optics system may comprise incident light beams, for example incident light beams entering the light-guiding part through the entrance face. The light beams following the optical path in an opposite direction through the optics system may comprise returning light beams, for example returning light beams entering the light-guiding part through the exit face. The array of returning light beams may comprise an array of light beams reflected by an object to be imaged (e.g. a teeth portion or segment).

The methods and apparatuses as described herein may comprise a detector for detecting an array of light beams. The detector may be arranged and/or configured to detect an array of returning light beams. The detector may comprise an array of detector elements. The detector may comprise a CCD, a camera, or a photodiode array, for example. The detector may comprise a spectrophotometer, for example.

The apparatuses as described herein may comprise a focus-shifting mechanism for shifting the focal plane of the optics system. For example, the focus-shifting mechanism may be configured to shift one or more lenses of the optics system along the optical axis. In many embodiments, the focus shifting detector may comprise a translation mechanism for translating the one or more lenses of the optics system.

The probe head as described herein may comprise a housing, in which the light-guiding part and/or the optics system are provided within the housing, for example. When a focus shifting mechanism is provided, the focus shifting mechanism may also be provided within the housing.

The probe head may comprise a part of a handheld device, for example. The optics system and/or the focus shifting mechanism may comprise part of the handheld device. In many embodiments, the handheld device is defined by a housing as described herein.

FIG. 1 schematically illustrates an example of an apparatus for dental confocal imaging of a teeth segment or teeth portion, in accordance with many embodiments. The teeth segment may comprise one tooth, a plurality of teeth, a tooth stump, and/or a portion or segment where one or more teeth are missing, for example. The apparatus may be used, for example, for intraoral imaging of teeth. Alternatively or additionally, imaging of a positive or negative teeth model may be performed employing this apparatus.

The illustrated apparatus comprises a light emitter 1 as a source of coherent light. As an example, the light emitter may be a laser source such as a semiconductor laser.

As indicated by the arrow shown, emitted light passes through a polarizer 2 such as a polarization filter to generate linearly polarized light.

The linearly polarized light passes through a beam expander 3, which may comprise a collimating lens so as to obtain a collimated light beam having a desired width or numerical aperture.

The beam expander 3 is followed by a beam splitter element 4, for splitting the beam into an array of light beams. The beam splitter element 4 in the form of diffraction or refraction optics may comprise a grating or a microlens array, for example.

In the illustrated embodiments, the light emitter 1 comprises a single light source from which the array of light beams is generated via the beam expander and the beam splitter element. As an alternative, the light emitter 1 may already comprise a plurality of light sources being arranged in form of an array. In these embodiments, the array of light beams is generated directly at the light emitter 1 so that a beam expander and/or beam splitter may be avoided. As an example, the array of light sources may be provided in the form of an array of laser sources, such as semiconductor lasers.

In general, the polarizer 2 may alternatively be arranged between the beam expander 3 and the beam splitter element 4, or even after the beam splitter element 4. The array of light beams, represented here, for ease of illustration, by a single line, passes through a beam splitter 5 in form of a semi-transparent mirror and enters optics system 6. The beam splitter element 5 may comprise a polarizing beam splitter, for example.

In many embodiments, the amount of polarization can be controlled so that the cumulative relative retardance of the components is ½ wavelength by the time the reflected beams leave the probe towards the beam splitter as described herein. The polarization components of the illumination light beam may undergo a relative phase shift of a quarter wavelength along the optical path between the entrance and exit faces as described herein, and the polarization components of the return light beam may undergo a relative phase shift of an quarter wavelength between the exit face and the entrance face along the return path, in order to provide a cumulative relative retardance of ½ wavelength. The cumulative relative retardance of ½ wavelength of the polarization components of the returning light beam provides a 90° rotation of the linearly polarized light of the return light exiting the probe relative to the linearly polarized light entering the probe.

The optics system 6 comprises a confocal lens arrangement operating in a telecentric or non-telecentric mode. A telecentric confocal optics avoids distance-introduced magnification changes and maintains the same magnification of the image over a wide range of distances in the direction along the optical axis. Optionally and with embodiments comprising a telecentric optics, an additional relay optics may be provided to maintain a desired numerical aperture of the beams.

The light beams coming from the light emitter 1 and propagating towards the sample to be imaged (e.g., a teeth segment) are called incident light beams, whereas light beams being reflected at the sample and propagating along the optical path of the incident light beams, but in an opposite direction, are called returning light beams.

After the optics system 6, the incident array of light beams enters a probe head 7. In particular, the array of light beams is coupled into a light-guiding part of the probe head via or through the light-guiding part's entrance face. Within the light-guiding part, each beam is reflected several times before it is coupled out via or through an exit face onto an object to be imaged, such as a teeth segment 8. In this way, an incident array of light beams is emitted towards the teeth segment 8, thus, resulting in an array of light spots on the teeth surface.

As also illustrated by one of the arrows between a tooth and the probe head, reflected light reenters the probe head 7, particularly its light-guiding part, via the exit face. In this way, each reflected/returning light beam travels along the optical path in an opposite direction as travelled by the incident light beams. Therefore, the returning light beams are also reflected several times within the light-guiding part of probe head 7, and pass through optics system 6 in inverse direction. At the semi-transparent mirror 5, the returned light beams are reflected towards imaging optics 9, comprising one or more lenses, followed by a pinhole array 10.

Then, the array of returning light beams impinges onto a detector 11, comprising an array of detector elements. For example, the detector 11 may be a CCD camera or a photodiode array. Each detector element or sensing element corresponds to a pinhole in the array 10.

The detector 11 is connected to a processing unit 12 where each light intensity measured in each of the detector elements is grabbed and analyzed.

The apparatus further comprises a control unit 13 being connected to the light emitter 1, as well as to a motor 14. Motor 14 is an example of a focus-shifting mechanism for shifting the focal plane of the optics system 6. In particular, motor 14 is coupled to the optics system 6 so as to shift or translate one or more lenses of the optics system along the optical axis. In this way, the focal plane location may be changed or shifted.

After receipt of a feedback signal that the location of the focal plane has changed (or that the one or more lenses have been shifted), control unit 13 triggers light emitter 1 to generate light pulses. Processing unit 12 will grab data representative of the light intensity as detected by detector 11 corresponding to the light pulse that was reflected at the teeth segment 8. This procedure will be repeated for a plurality of locations for the focal plane.

As outlined in detail in WO 00/08415, the entire disclosure of which is incorporated herein by reference, the surface topology of the imaged object (e.g., the teeth segment) is determined by determining the focal plane location for which, for a particular pixel, the light intensity is maximal. In this way, a three-dimensional representation of the object, e.g., the teeth segment, may be obtained; it may be displayed and/or further processed.

The array of light beams may comprise light beams having different wavelengths. For this purpose, the light emitter 1 may comprise different light sources emitting light of different wavelengths. In embodiments with an array with beams of different wavelengths, the detector may comprise a spectrophotometer with color resolution, for example. Examples for spectrophotometers include a three chip CCD camera or the use of a Bayer mask over a monochrome CCD or other light sensor.

By using light components or light beams with different wavelengths, each being focused simultaneously on a different focal plane, the time for imaging may be reduced as different focal plane ranges can be simultaneously measured.

The probe head 7 may comprise a housing. For example, both the optics system 6 and the light-guiding part may be provided within such a housing. The housing may be configured as a handheld device so that the light-guiding part and/or optics system 6 and/or motor 14 are included in the handheld device.

FIG. 2 schematically illustrates a top view of a probe head 7, in accordance with many embodiments. The probe head 7 has a light-guiding part with an entrance face 15, a schematic plan view of which is illustrated in FIG. 3. FIG. 4 schematically illustrates a cross-sectional view of the probe head through line A-A, i.e., parallel to the symmetry plane, which extends along the optical axis of the light-guiding part and is perpendicular to the light-guiding part's lower sidewall.

Light coming from the light emitter and the optics system enters the light-guiding part via the entrance face 15 at an angle of about 90°, such as substantially normal to the entrance face 15. The incident light can be linearly polarized. In the embodiments illustrated schematically in FIG. 3, the polarization vector 20 has a non-zero angle with respect to the symmetry plane of the probe head and the light-guiding part, respectively. In many embodiments, the polarization vector 20 is tilted by an angle of about 45°, for example. The cross in FIG. 3 shows a coordinate system, wherein the symmetry plane is parallel to the vertical axis.

As schematically illustrated in FIG. 4, the light-guiding part is arranged and light is coupled into the light-guiding part in such a way that each light beam entering the light-guiding part via the entrance face 15 is reflected at the sidewalls. In the illustration of FIG. 4, only one beam is indicated by a single line, which is reflected three times before exiting the light-guiding part via the exit face 16. A person of ordinary skill in the art will recognize that a plurality of light beams can be transmitted and received along the light-guiding part in a manner similar to the beam shown in FIG. 4.

In many embodiments, a first reflection takes place at an upper sidewall 17, adjoining the entrance face 15, and being arranged at an acute angle with respect to the entrance face 15. The second reflection may occur at lower sidewall 18, also adjoining the entrance face 15 and being arranged at an obtuse angle with respect thereto. The last reflection may occur at the end sidewall 19, adjoining both the upper and the lower sidewalls. The exit face 16 can be part of the lower sidewall 18. End sidewall 19 may comprise a mirror, which may be obtained by a suitable coating of the corresponding surface of the light-guiding part, for example. The exit face 16 may correspond to a perpendicular projection of the end sidewall 19 onto the lower sidewall 18.

In many embodiments, the light-guiding part comprises a stiff, for example rigid, one-piece body. For example, the light guiding part may comprise a glass body or a body composed of a transparent resin. The first and second reflections at upper sidewall 17 and lower sidewall 18 may result from total internal reflection, for example. In many embodiments, the angle of incidence and index of refraction are arranged and configured such that the angle of incidence is above a critical angle such that a complete reflection takes place because of the difference in the refractive indices of the sidewall and the surrounding medium, which can be air or another medium. The total internal reflection may comprise one or more of attenuated total internal reflection, frustrated total internal reflection, or total internal reflection, for example.

The light-guiding part is configured in such a way that the polarization of the light beams entering the light-guiding part via the entrance face 15 is changed along the optical path through the light-guiding part. In the embodiments illustrated in FIG. 4, the light beam (which had a linear polarization upon entry via the entrance face 15) exiting at exit face 16 shows one or more of an elliptical polarization or a circular polarization, for example.

Based on the teachings provided herein, a person of ordinary skill in the art can configure the light-guiding part to provide the change of the polarization as described herein with a material of the light-guiding part and/or a retardance coating on one or more of the sidewalls of the light-guiding part where reflection takes place as described herein, for example with reference to FIG. 5.

In many embodiments, the polarization of a light beam or a light ray comprises two polarization components perpendicular to each other. In many embodiments, the polarization vector comprises two vector components being perpendicular to each other. The polarization can be split into a "p" component and an "s" component. The p component is the component parallel to the plane of incidence, wherein the plane of incidence is the plane that contains the propagation direction of a ray being incident on the surface and the reflected and possibly transmitted rays, for example. In many embodiments, the plane of incidence is parallel to the symmetry plane of the probe head and the light-guiding part, respectively.

The s component is the component perpendicular to the plane of incidence. The retardance coatings on the one or more sidewalls can be configured such that one of the two polarization components (compared to the other of the two polarization components) is retarded by an odd multiple of a quarter of the wavelength (or by an odd multiple of $\pi/2$ or 90°) along the path from the entrance face to the exit face, for example.

FIG. 5 schematically illustrates a cross-sectional view of the probe head 7, wherein the cross-section plane is parallel to the symmetry plane of the probe head or light-guiding part, similarly to the embodiments of FIG. 4. As in the example of FIG. 4, the probe head 7 has a light-guiding part with an entrance face 15 and an exit face 16, as well as an upper sidewall 17, a lower sidewall 18, and an end sidewall 19.

Alternatively or in combination a transparent cover sheet 21 can be provided as shown in FIG. 5, in which the transparent coversheet is arranged at a distance from the exit face 16. This cover sheet 21, which may comprise a plate, may be exchangeable for hygienic reasons, and may also be provided in accordance with embodiments described herein such as with reference to FIG. 4, for example.

In the embodiments illustrated in FIG. 5, the light-guiding part of the probe head 7 can be longer than in the embodiments of FIG. 4, for example, resulting in five reflections of the light beams before exiting via the exit face 16. Any odd number of reflections can be provided in accordance with embodiments disclosed herein.

In many embodiments such as described herein with reference to FIG. 5, the light-guiding part is made of glass, which is obtained from Schott AG under the trade name N-BK7, for example. To achieve a desired change of polarization, the lower sidewall 18 can be coated with a retardance coating, for example, and the upper sidewall 17 can remain uncoated, for example.

In some embodiments, the coating comprises a plurality of alternating layers of the following materials: titanium oxide ($Ti_3O_5$, abbreviated as "H", high index), silicon oxide ($SiO_2$, abbreviated as "L", low index), and tantalum oxide ($Ta_2O_5$, abbreviated as "M", medium index). The plurality of layers may comprise a low index layer, a high index layer and a medium index layer. The low index layer may comprise a plurality of non-adjacent low index layers; the high index layer may comprise a plurality of non-adjacent high index layers; and the medium index layer may comprise a plurality of non-adjacent medium index layers. These layers can be deposited in the following order on the glass: air-LHLHLMLM-glass, for example. The total thickness of the coating can be about 450 nm, for example.

In many embodiments, the end sidewall 19 comprises a mirror coating such as a metallic layer, for example a silver layer. The mirror on the front end can be coated with a suitable film as described herein to provide the full ¼ wave retardation, when complemented with the existing retardation induced by TIR in the other surfaces, for example.

Table 1 shows the phase retardance between the p and s components for a specific angle of incidence (AOI) of a light ray with a wavelength of 680 nm. At the upper and lower sidewalls, total internal reflection takes place whereas the reflection at the end sidewall results from the mirror coating. Due to the above-described coating at the lower sidewall, the total reflection at the lower sidewall is affected in such a way that the phase retardance through the light-guiding part sums up to 450°.

TABLE 1

Phase retardance as a function of AOI

| Reflection/transmission wall | Central ray AOI [deg] | Phase retardance [deg] |
|---|---|---|
| Entrance face | 90.00 | 0 |
| Upper sidewall, first reflection | 64.40 | 143.9 |
| Lower sidewall, first reflection | 62.40 | 75.5 |
| Upper sidewall, second reflection | 60.40 | 139.5 |
| Lower sidewall, second reflection | 58.40 | 91.1 |
| End sidewall | 29.20 | 0 |
| Exit face | 90.00 | 0 |

As can be seen, there is no phase retardance or change in the polarization when the beam passes through the entrance and through the exit face. Little or no phase retardance takes place upon reflection at the metallic mirror.

The phase retardance between the p and s components at the first four reflection points at the upper and lower sidewalls sums up to 450° or 5 π/2, i.e., an odd multiple of π/2 or of a quarter of the wavelength (λ/4). As a consequence, for a light beam being linearly polarized (wherein the polarization vector is tilted with respect to the symmetry plane of the probe head or the light-guiding part) upon entry of the light-guiding part through the entrance face 15, an elliptical polarization may be achieved upon exit through the exit face.

Other coatings may be used as well to obtain a desired phase retardance. Furthermore, the phase retardance at the different reflection points or regions may be set differently. For example, instead of using a metallic mirror coating, a dielectric mirror coating (e.g., comprising multiple dielectric layers) may be used, which can provide a non-zero phase retardance at the end sidewall.

As another example in accordance with embodiments described herein, by employing a suitable coating design, a coating can be deposited on both the upper and the lower sidewall. In many embodiments, the cumulative phase retardance of all reflections along the optical path within the light-guiding part sums up to an odd multiple of π/2 corresponding to an odd multiple of a quarter of the wavelength.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An apparatus for dental imaging, the apparatus comprising:
    an illumination module for generating a light beam travelling an optical path, the light beam having a wavelength;
    a probe head comprising a light-guiding part having,
        an entrance face,
        an exit face,
        a coated sidewall comprising a retardance coating to reflect the light beam along the optical path with a first total internal reflection having a first retardance of a non-integer multiple of a quarter of the wavelength, said first retardance comprising a retardance from the retardance coating, and
        an uncoated sidewall without a retardance coating to reflect the light beam along the optical path with a second total internal reflection having a second retardance of a non-integer multiple of a quarter of the wavelength; and
    an optics system to direct the light beam along the optical path to enter the light guiding part via the entrance face, travel along the optical path extending between the entrance face and the exit face, and exits the light-guiding part via the exit face,
    said first and second retardances being in amounts such that the light-guiding part provides a total retardance of an odd multiple of the quarter of the wavelength along the optical path extending from the entrance face to the exit face,
    wherein each of the first retardance, the second retardance, and the total retardance is a retardance to a first polarization component relative to a second polarization component of the light beam traveling along the optical path.

2. The apparatus according to claim 1, wherein the light-guiding part comprises a transparent body and wherein the light beam comprises a linearly polarized light beam comprising the first polarization component and the second polarization component, wherein the first polarization component and the second polarization component are perpendicular to each other.

3. The apparatus according to claim 1, wherein the light-guiding part comprises a one-piece body.

4. The apparatus according to claim 1, wherein the light-guiding part comprises an upper sidewall, a lower sidewall and an end sidewall, the upper sidewall adjoining the entrance face, the upper side wall arranged at an acute angle with respect to the entrance face, the lower sidewall adjoining the entrance face, the lower sidewall arranged at an obtuse angle with respect to the entrance face, the end sidewall adjoining the upper sidewall and the lower sidewall, and the end sidewall arranged at an acute angle with respect to the entrance face and/or the exit face, and wherein one of the upper sidewall and the lower sidewall is the coated sidewall, and the other is the uncoated sidewall.

5. The apparatus according to claim 4, wherein the end sidewall comprises a mirror.

6. The apparatus according to claim 4, wherein an angle extending between the entrance face and the lower sidewall is within a range between 90° and 125°.

7. The apparatus according to claim 1, wherein:
    the light beam generated by the illumination module comprises an array of light beams; and
    the optics system provides confocal focusing of the array of light beams.

8. The apparatus according to claim 7, wherein the light-guiding part is bounded by sidewalls and the light-guiding part is arranged such that each light beam entering the light-guiding part through the entrance face is reflected at the sidewalls an odd number of times, the odd number of times comprising three times or five times, before exiting through the exit face.

9. The apparatus according to claim 7, wherein the illumination module comprises a single light emitter.

10. The apparatus according to claim 7, wherein the illumination module comprises a plurality of light emitters.

11. The apparatus according to claim 7, further comprising a polarizer for linearly polarizing a light beam, wherein the polarizer is arranged along the optical path between the illumination module and the probe head and between the illumination module and the optics system.

12. The apparatus according to claim 7, further comprising a polarizing beam splitter being arranged along the optical path between the illumination module and the optics system such that the array of light beams from the illumination module passes through the polarizing beam splitter and a returning array of light beams from the optics module is reflected.

13. The apparatus according to claim 7, further comprising a detector for detecting an array of light beams.

14. The apparatus according to claim 7, further comprising a focus shifting mechanism for shifting the focal plane of the optics system.

15. The apparatus according to claim 14, wherein the focus shifting mechanism is configured to shift one or more lenses of the optics system along an optical axis.

16. The apparatus according to claim 1, wherein angles of surfaces of the light guiding part are arranged to provide a first portion of the retardance and one or more coatings on one or more of the surfaces comprises a plurality of layers configured to provide a second portion of the retardance, wherein the first portion combined with the second portion provides a combined total relative retardance between the entrance face and the exit face comprising the odd integer multiple of the quarter of the wavelength.

17. The apparatus according to claim 16, wherein the first portion of the retardance comprises a first non-integer multiple of the quarter of the wavelength and the second portion of the retardance comprises a second non-integer multiple of the quarter of the wavelength and wherein one or more coatings comprises a plurality of layers comprising a low index layer, a high index layer and a medium index layer.

18. The apparatus according to claim 1, wherein the optics system directs the light beam along the optical path such that the beam enters the entrance face at an angle of between 85 and 95 degrees.

19. The apparatus according to claim 18, wherein the beam enters the entrance face at an angle of about 90 degrees.

* * * * *